United States Patent [19]
Shaw

[11] Patent Number: 5,415,545
[45] Date of Patent: May 16, 1995

[54] DENTAL IMPLANT SYSTEM
[75] Inventor: Leon Shaw, Delray Beach, Fla.
[73] Assignee: Minimrix Implant Technology, Boca Raton, Fla.
[21] Appl. No.: 17,063
[22] Filed: Feb. 12, 1993
[51] Int. Cl.[6] .......................... A61C 8/00; A61C 13/12; A61C 13/225
[52] U.S. Cl. ..................................... 433/173; 433/172
[58] Field of Search ............... 433/172, 173, 174, 175, 433/176

[56] References Cited
U.S. PATENT DOCUMENTS

| | | | |
|---|---|---|---|
| 4,531,915 | 7/1985 | Tatum, Jr. | 433/176 X |
| 5,004,420 | 4/1991 | Soderberg | 433/172 |
| 5,092,771 | 3/1992 | Tatum, III | 433/173 |
| 5,122,059 | 6/1992 | Durr et al. | 433/173 |
| 5,174,755 | 12/1992 | Fukuda | 433/173 |

FOREIGN PATENT DOCUMENTS 3524556 1/1987 Germany .............................. 433/172

Primary Examiner—Gene Mancene
Assistant Examiner—Nicholas D. Lucchesi
Attorney, Agent, or Firm—M. K. Silverman

[57] ABSTRACT

A dental implant system includes an implant having its external geometry proportioned for securement within a human mandible. A junction between the implant and a complemental abutment of a dental prosthesis includes a journal that is defined by two bearing surfaces respectively preceding and following a threaded part of the junction. A longitudinal internal bore of the implant begins at a proximal open end of the implant and extends to a closed distal end, the bore includes the threaded part of the junction and is of substantially uniform diameter and pitch. A distal end of the bore defines one of the bearing surfaces and a proximal end of said bore defines the other bearing surface. The abutment of the dental prosthesis includes a male element which is complemental in all respects to the threaded portion of the bore and the bearing surfaces internal to the bore of the implant.

4 Claims, 3 Drawing Sheets

DENTAL IMPLANT SYSTEM

BACKGROUND OF THE INVENTION

The present invention relates to the subject of dental implants and, more particularly, a system for the securement of the prosthetic component of a dental system to a mandible implant.

In the prior art of dental implant technology, a long-standing problem has been that of assuring that the dental prosthesis, once secured to the implant, will not shift relative thereto. As is shown in the FIG. 1 view of the prior art, it has been well-known to employ what is termed a hex-type connection for purposes of securement of the abutment of a dental prosthesis to the implant body. This arrangement, as is more fully described in the Detailed Description of the Invention, employs a long threaded interface which after securement between the abutment and the implant, does not afford any means for the relief of pressures, stresses and forces upon the threaded interface between the abutment and the implant, It has, over the years during which dental implants have been used, been determined that the threads of such an implant system (which are typically formed of titanium) become exceedingly brittle such that, in the absence of a mechanism for the release or diffusion of stresses, strains and the like, chipping and abrading of the threaded junction will inevitably occur.

In addition to prior art systems of the type of FIG. 1, there has, further, been employed the so-called bevel junction which is shown in the view of FIG. 2, Although this geometry affords some advantages with respect to the uppermost aspects thereof, it does not address the basic problem of the implant-abutment junction, namely, that of the extended threaded interface which is vulnerable to chipping, abrasion, other forms of fracturing, metal transfer, and generalized material migration. These factors mean that such a junction cannot efficiently diffuse the prosthetic stresses between the abutment and the implant which are an aspect of normal use of any such system, This circumstance operates to increase the probability of external or internal failure of the entire prosthesis-implant system.

In addition, as can be well imagined, the abutment-/implant interface will, over the estimated ten-year life of a prosthesis-implant system, be subject to not only stresses, strains and impacts but, as well, to metabolically-generated organic molecules that are capable of entering and attacking the junction between the abutment and the implant at the line at which said junction, which is near to the mandible into which the implant, has been secured.

This invention has, accordingly, developed in response to the above stated problems of efficiency and durability of prior art prosthetic-implant systems.

SUMMARY OF THE INVENTION

The instant invention constitutes a dental implant system comprising an implant having its external geometry proportioned for securement within a human mandible. A junction between the implant and its complemental abutment of a dental prosthesis comprises journal means that are defined by proximal and distal bearing surfaces respectively preceding and following a threaded part of the junction. A longitudinal internal bore of the implant begins at a proximal open end of the implant and extends to a closed distal end thereof, said bore having said threaded part as an intermediate portion of substantially uniform diameter and pitch. A distal end of said bore defines said distal bearing surface and a proximal end of said bore defines said proximal bearing surface. The abutment of the dental prosthesis includes a male element which is complemental in all respects to said threaded portion and bearing surfaces of said longitudinal internal bore of said implant.

In addition, an upper, proximal-most portion of the implant and the abutment may take the form of either a so-called hex-head geometry or a bevel-head geometry which is in the nature of a conical section. By reason of the provision of said journal means, microscopic rotation and counter-rotation of the threaded portion of the implant-abutment interface may occur, thus providing a means for distribution of the prosthetic stresses and impacts to which the system will, in the course of normal use, become subject.

It is accordingly an object of the present invention to provide a dental implant system having a prosthesis abutment-implant body interface that will minimize the problems of fracturing, abrasion, material migration and metal transfer along the junction between said abutment and implant body.

It is another object of the invention to provide a dental implant system of the above type in which the possibility of harmful shifting of the abutment relative to the implant body is reduced.

It is a further object to provide a dental implant system in which the abutment-implant junction affords a more efficient distribution of prosthetic stress than exists in the prior art, It is a yet further object of the invention to provide a dental implant system in which abutment-implant junction will provide a higher probability of long term success than is the case with prior art junctions or interfaces.

The above and yet other objects and advantages will become apparent from the hereinafter set forth Brief Description of the Drawings, Detailed Description of the Invention and Claims appended herewith.

DETAILED DESCRIPTION OF THE INVENTION

Figure 1:
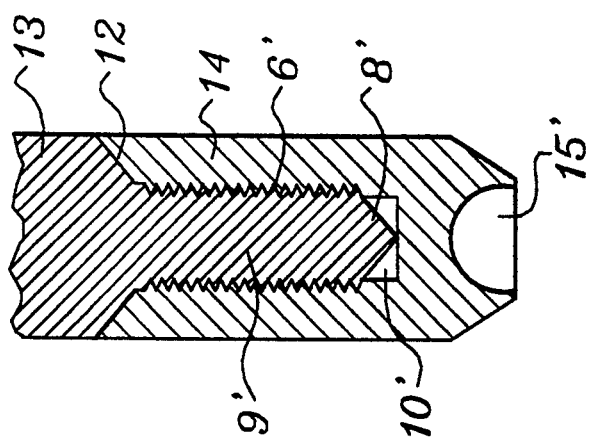
FIG. 1 is a longitudinal diametric cross-sectional view of a prior art implant-abutment junction employing a hex-head proximal portion.
Figure 2:
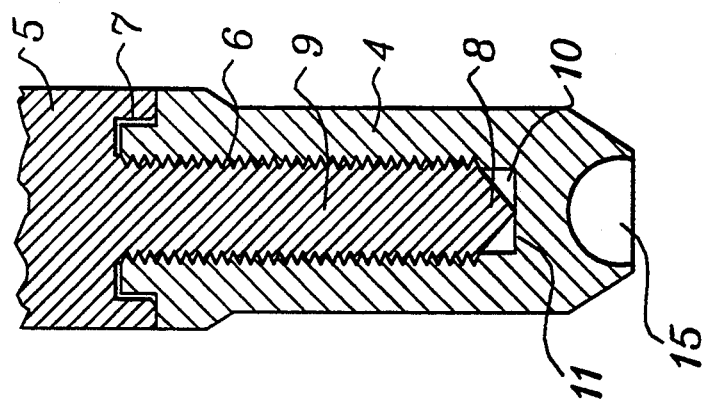
FIG. 2 is a longitudinal diametric cross-sectional view of a prior art implant-abutment junction employing a bevel-head proximal portion.

With reference to the views of FIGS. 1 and 2 there is shown two prior art dental implant systems employing respectively hex-head and bevel-head prosthesis-abutment junctions. With reference to FIG. 1 it may be seen that the female geometry of implant 4 meets with the male geometry of abutment 5 to form a threaded longitudinal junction 6 which extends from proximal hex-head junction 7 to a tip 8 at the distal end of male element 9 of the abutment 5. Also shown is void 10 which exists about said tip 8 and above distal surface 11 of the longitudinal threaded bore within implant 4.

With reference to FIG. 2 there is shown another prior art junction known as a bevel-head connection. This differs from the above-described hex-head junction only in the bevel-shaped geometry of junction 12 between abutment 13 and implant 14. In other respects, the geometry of the embodiment of FIG. 2 is similar to that of FIG. 1, in that, particularly, the same long longitudinal threaded interface 6' is provided as is tip 8' of male element 9'. Accordingly, in the embodiment of the prior art of FIG. 2, as in the embodiment of the prior art of FIG. 1, there does not exist any means for relief of prosthetic stresses across the long threaded junction 6' between the implant 14 and the threaded male element 9' of abutment 13. That is, should this junction become subject to severe stress, strain, force or impact having a rotational component (which is the case with most such effects), the result will be a fracture, crack, abrasion or the like along either threaded junction 6 or 6' or an actual break of tip 8 or 8' with chipped material resultingly falling into void 10 or 10'.

It is noted that semicircles 15 and 15' at the bottom of FIGS. 1 and 2, are so-called blood collection areas which bear no relationship to the inventive aspects of the invention as described below.

Figure 5:
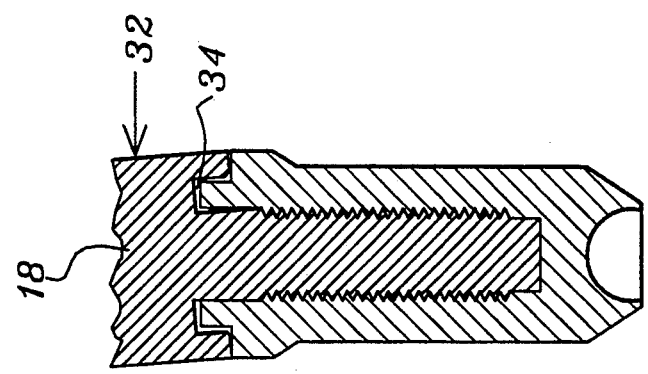
FIG. 5 is a view of FIG. 4 showing the effect of a rotational component of force thereon.
Figure 4:
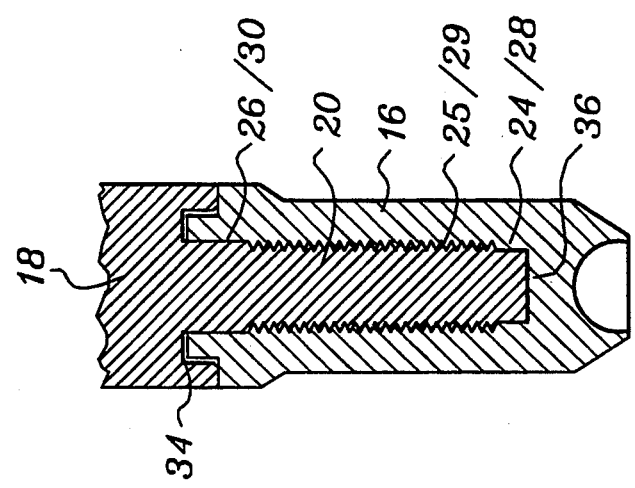
FIG. 4 is an assembly view of FIG. 3.
Figure 3:
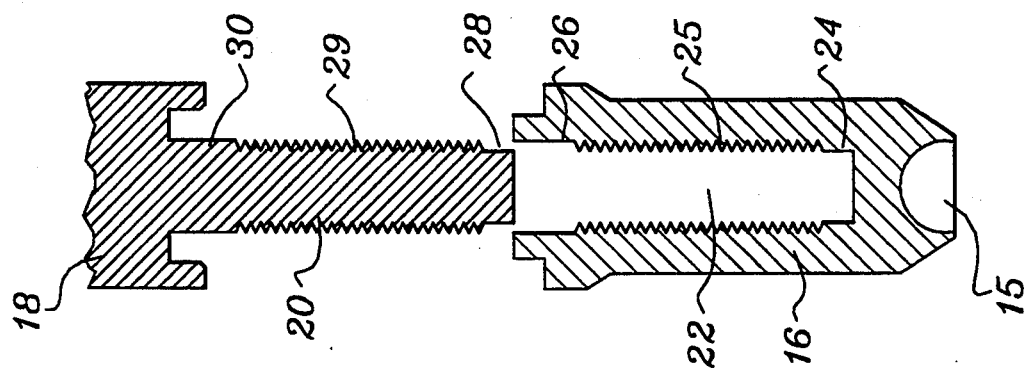
FIG. 3 is an exploded view of a hex-head embodiment of the inventive system.

With reference of the views of FIGS. 3 thru 5 there is shown a first embodiment of the instant invention in which there may, more particularly, be seen an implant 16 and prosthetic abutment 18 having, depending integrally therefrom, an elongated threaded male member 20 which is complemental in all respects to a longitudinal bore 22 of the implant 16. Said longitudinal bore 22 may be seen to, more particularly, include a distal bearing surface 24 which follows, and along substantially the entire length of said bore 22, threading 25 of the implant 16 and a proximal bearing surface 26 which precedes said threading 25 of bore 22.

Similarly, said male element 20 of the abutment 18 may be seen to include a distal bearing surface 28, a threaded surface 29, which extends substantially the length of said male element and, co-axial with said bearing surface 28, a proximal bearing surface 30 which depends integrally from the top portion of abutment 18.

With reference to FIG. 4, there is shown the assembled hex-head embodiment of the instant invention. Therefrom, it may be appreciated that distal bearing surfaces 24 and 28, on the one hand, and proximal bearing surfaces 26 and 30, on the other hand, operate to define a journal means by which rotational components of prosthetic stress, strain, impact, or forces, such as force 32 shown in FIG. 5, will have the effect of causing a microscopic rotation of abutment 18 relative to implant 16 about the axis of bore 22. It is to be appreciated that an upper junction 34 between abutment 18 and implant 16 also comprises a part of journal means. The resultant effect of such forces, when of a microscopic rotation occurs, is to cause a slight compression at distal interface 36 at the distal end of male element 20 and the distal end of longitudinal bore 22. Conversely, if the direction of the force 32 is counterclockwise, the effect will simply be that of creating a microscopic opening at distal interface 36. The result of these phenomena will be to allow for efficient distribution of prosthetic stress and the like and, thereby, to minimize the possibility of fracturing, abrasion, metal transfer or material migration across the threaded junction defined by said threaded surfaces 25 and 29, With reference to the views of FIGS. 6 thru 8, there is shown an alternate embodiment of the instant invention known as a bevel-head connection between an implant 36 and a prosthetic junction 38. More particularly, there is in Figs, 6 thru 8 shown a second embodiment of the inventive dental implant system which includes said implant 36 which is externally proportioned for securement within the human mandible, Said implant 36 includes a longitudinal internal bore 40 which begins at a proximal open end 42 of the implant and extends to a closed distal end 44 thereof. Most of longitudinal bore 40 is defined by cylindrical circumferential threading 46. However, distally preceding threading 46 is, between distal end 44 of bore 40 and the distal-most beginning 52 of bore threading 46, a distal bearing surface 48 which is analogous in structure to said distal bearing surface 24 of implant 16 of the embodiment of FIGS. 3 thru 5, Immediately above proximal-most end 54 threading 46 is a cylindrical female bearing surface 55 and a partial conical section female bearing surface 56. Accordingly, it may be seen that said proximal bearing surfaces 55 and 56 are an extension of the proximal open end 42 or the implant 36.

Figure 8:
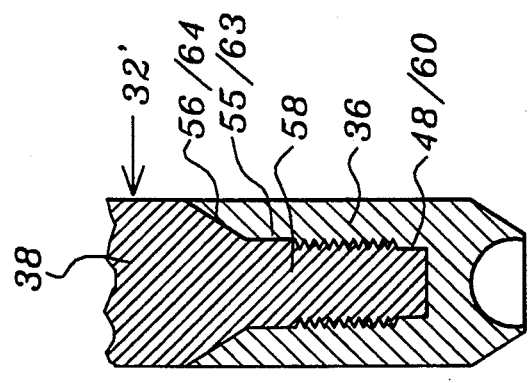
FIG. 8 is a view of FIG. 6 showing the effect of a rotational component of force thereon.
Figure 7:
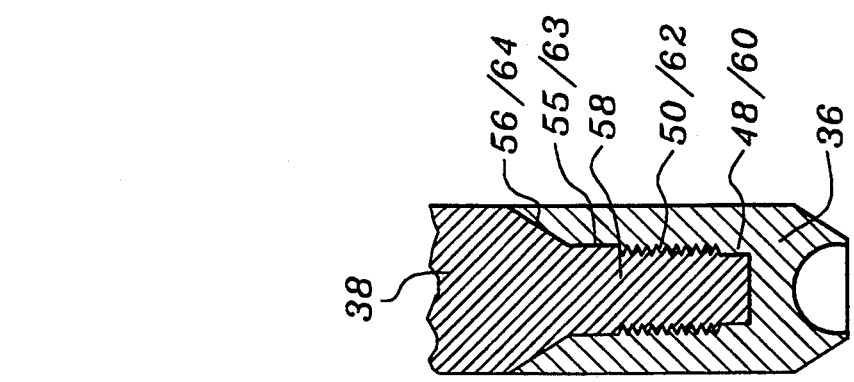
FIG. 7 is an assembly view of FIG. 6.
Figure 6:
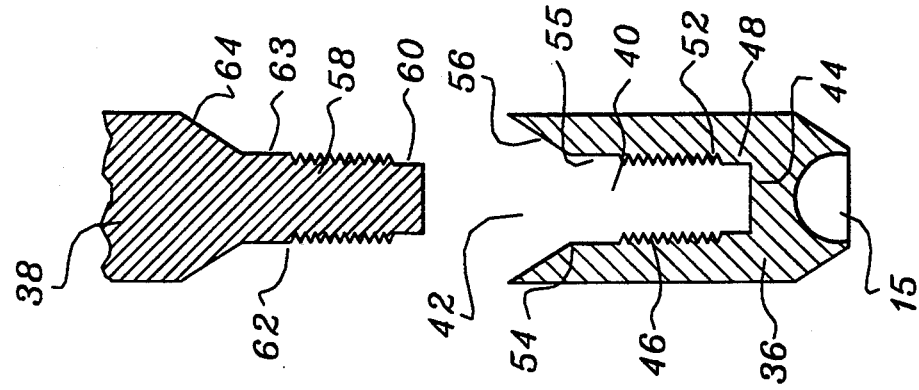
FIG. 6 is an exploded view showing a bevel-head junction embodiment of the inventive system.

With reference to the abutment 38, shown in the exploded upper portion of FIG. 6, the external geometry of said abutment may be seen to be essentially complemental to that of the above-described implant 36 of the embodiment of FIGS. 6 thru 8. More particularly, said abutment includes a male element 58 having, at a distal end thereof, a distal bearing surface 60 followed by a threaded circumferential surface 62 conforming in pitch and diameter to said threaded surface 46 or to bore 40 of implant 36, and proximal bearing surfaces 63 and 64, taking the form of male cylindrical and partial conical sections which are complemental in all respects to said proximal bearing surfaces 55 and 56 of the implant 36, With reference to the view of FIG. 7, the elements of the second embodiment are seen in assembled operational view, Therein, the embodiment of FIG. 6 thru 8 may be seen to differ from the embodiment of FIGS. 3 thru 5 in the geometry of the proximal bearing surfaces 56/64. In other words, in the embodiment of FIGS. 3 thru 5, both bearing surfaces are cylindrical and are mutually co-axial, in the embodiment of FIGS. 6 thru 8, the distal bearing surfaces 48/60 are cylindrical while the proximal bearing surfaces are partly conical. It has been found that the embodiment of FIGS. 6 thru 8 offers certain advantages over the embodiment of FIG. 3 thru 5 in that the proximal conical bearing surfaces 56/64, when impacted by an external rotational force component 32', more efficiently diffuse such prosthetic stress and, particularly, will do so with reduced metal transfer and material migration across the proximal interface of the system. In other words, it has been found that in the hex-head interface, described with respect to the embodiment of FIGS. 3 thru 5, an abrupt change in direction of the abutment-implant interface in area 34 (see FIGS. 4 and 5) increases the possibility of chipping and abrasion along such interface and, as well, increases the possibility of attack of such interface by organic molecules to which the system is subject during use.

With further reference of the embodiment of FIGS. 6 thru 8, it is to be understood that the combination of distal bearing surfaces 48 and 60 on the one hand, and proximal bearing surfaces 55/63 and 56/64 on the other hand, operate to define a journal means which is otherwise analogous to the above described journal means with reference to the embodiment of FIGS. 3 thru 5.

Figure 9:
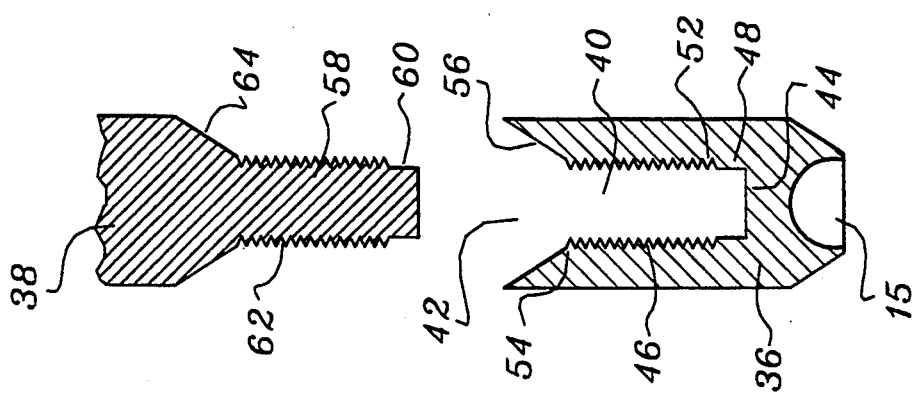
FIG. 9 is an assembly view of another bevel-head junction embodiment of the invention.

With respect to the exploded view of FIG. 9 there is shown a further embodiment in which the proximal bearing surfaces of the system consist only of complemental female/male conical sections 56/64.

Accordingly, while there has been shown and described the preferred embodiment of the present invention, it is to be understood that the invention may be embodied otherwise than is herein specifically shown and described and that within said embodiments certain changes may be made in the form and arrangements of the parts without departing from the underlying ideas or principles of this invention as set forth in the claims appended herewith.

Having thus described my invention, what I claim as new, useful and non-obvious and, accordingly, secure by Letters Patent of the United States is:

1. A dental implant system, comprising:
 (a) an implant externally proportioned for securement within a human mandible, said implant including a longitudinal internal bore beginning at a proximal open end of said implant and extending longitudinally to a closed distal end situated substantially at a distal end of said implant thereof, said bore having an unthreaded distal portion comprising a distal bearing surface and an unthreaded proximal bearing surface, comprising said open end thereof, said bore further having, between said distal and proximal bearing surfaces, a threaded portion of substantially uniform diameter and pitch; and
 (b) an abutment of a dental prosthesis, the abutment having a male element, with an external surface thereof having a distal bearing surface unthreaded and fully complemental to said distal bearing surface of said implant,
 a proximal bearing surface unthreaded and complemental to said proximal bearing surface of said implant, and a threaded portion of uniform diameter and pitch, extending substantially the length of said male element, complemental to said threaded portion of said bore of said implant,
whereby, upon complete threaded securement of said prosthesis abutment to said implant, said distal and proximal bearing surfaces will co-act to define journal means capable of diffusing prosthetic stresses to which the system will, in the course of normal use, become subject.

2. The system as recited in claim 1 in which said proximal and distal bearing surfaces both comprise complemental male and female cylindrical segments.

3. The system as recited in claim 2 in which said proximal bearing surfaces include complemental male and female conical sections.

4. The system as recited in claim 1 in which said proximal bearing surfaces comprise complemental male and female conical sections and said distal bearing surfaces comprise complemental male and female cylindrical segments.

* * * * *